(12) United States Patent
Asano et al.

(10) Patent No.: US 7,857,759 B2
(45) Date of Patent: Dec. 28, 2010

(54) EXTRACTION DEVICE, ANALYZER, EXTRACTION METHOD, AND ANALYSIS METHOD

(75) Inventors: Kaoru Asano, Kobe (JP); Yasunori Maekawa, Miki (JP); Kennichi Sawa, Amagasaki (JP); Toshiyuki Sato, Nishinomiya (JP); Seiki Okada, Kobe (JP)

(73) Assignee: Sysmex Corporation (JP)

( * ) Notice: Subject to any disclaimer, the term of this patent is extended or adjusted under 35 U.S.C. 154(b) by 130 days.

(21) Appl. No.: 10/810,412

(22) Filed: Mar. 25, 2004

(65) Prior Publication Data
US 2004/0193219 A1  Sep. 30, 2004

(30) Foreign Application Priority Data
Mar. 26, 2003  (JP) .............................. 2003-086401

(51) Int. Cl.
*A61B 5/00* (2006.01)
(52) U.S. Cl. .................. 600/365; 600/345; 600/347; 604/20
(58) Field of Classification Search ............... 600/345, 600/347, 365; 604/20
See application file for complete search history.

(56) References Cited

U.S. PATENT DOCUMENTS

| | | | | |
|---|---|---|---|---|
| 5,279,543 A | * | 1/1994 | Glikfeld et al. ............... 604/20 |
| 5,771,890 A | * | 6/1998 | Tamada ....................... 600/347 |
| 6,144,869 A | * | 11/2000 | Berner et al. ............... 600/347 |
| 6,180,416 B1 | | 1/2001 | Kurnik et al. |
| 6,201,979 B1 | * | 3/2001 | Kurnik et al. ............... 600/345 |
| 6,356,776 B1 | | 3/2002 | Berner et al. |
| 6,391,643 B1 | | 5/2002 | Chen et al. |
| 6,438,414 B1 | * | 8/2002 | Conn et al. ................... 604/20 |
| 6,736,777 B2 | * | 5/2004 | Kim et al. .................... 600/365 |
| 2002/0058936 A1 | * | 5/2002 | Avrahami et al. ............. 606/41 |
| 2003/0120138 A1 | * | 6/2003 | Kurnik et al. ............... 600/345 |
| 2003/0199745 A1 | * | 10/2003 | Burson et al. ............... 600/347 |
| 2003/0208114 A1 | * | 11/2003 | Ackerman .................. 600/347 |
| 2004/0167418 A1 | * | 8/2004 | Nguyen et al. .............. 600/513 |
| 2004/0193089 A1 | * | 9/2004 | Fischer et al. ................. 602/48 |
| 2004/0230227 A1 | * | 11/2004 | Avrahami et al. .............. 607/3 |

FOREIGN PATENT DOCUMENTS

| WO | WO 96/00110 | 1/1996 |
|---|---|---|
| WO | WO 97/30628 | 8/1997 |
| WO | WO 97/30749 | 8/1997 |

* cited by examiner

*Primary Examiner*—Patricia C Mallari
*Assistant Examiner*—Karen E Toth
(74) *Attorney, Agent, or Firm*—Brinks Hofer Gilson & Lione

(57) ABSTRACT

Extraction device for extracting an analyte from living tissue through skin are described that include: (a) a first electrode part having a contact area with the skin of less than about 50 $mm^2$; (b) a through-current electrode part; and (c) a power supply part for supplying electrical energy to the first electrode part and the through-current electrode part, and for extracting an analyte in the first electrode part. Analyzers, extraction methods, and analysis methods are also described.

12 Claims, 18 Drawing Sheets

EXTRACTION DEVICE, ANALYZER, EXTRACTION METHOD, AND ANALYSIS METHOD

RELATED APPLICATIONS

This application claims priority under 35 U.S.C. §119 to Japanese Patent Application No. 2003-086401, filed Mar. 26, 2003.

FIELD OF THE INVENTION

The present invention relates to an extraction device for extracting an analyte in living tissue through the skin, to an analyzer for analyzing the analyte, and to extraction and analysis methods. More particularly, the present invention relates to an extraction device for extracting an analyte in living tissue through the skin noninvasively or minimally invasively, to an analyzer for analyzing the analyte, and to extraction and analyzing methods.

BACKGROUND

In clinical examinations, the presence and quantity of substances in collected blood samples are typically assayed. Diabetics measure their own blood sugar value several times each day, and determine their insulin dosage based on the measured value so as to self-manage their blood sugar level in determining food-intake restrictions, amount of exercise, and the like. Normally, the measurement of a blood sugar value is taken from blood samples collected using a puncturing tool or the like, which causes physical discomfort and burden for the patient. From this perspective, a simple examination that neither overburdens the patient nor requires blood collection would be very desirable.

In response to this demand, methods have been developed for extracting analyte in living tissue noninvasively and without collecting blood, and for measuring the amount and concentration of the analyte. Reverse iontophoresis is an example of such an assay method.

Reverse iontophoresis involves extracting an analyte through the skin by applying electrical energy to the skin (for example, see: U.S. Pat. No. 5,279,543 and International Patent Publication No. 96/000110).

Assay methods and devices using reverse iontophoresis have certain disadvantages, however, inasmuch as the quantity of extracted analyte is not stable until a lengthy time has elapsed after the initial application of electrical energy on the skin (i.e., start of current flow). For example, a Gluco Watch from Cygnus Incorporated requires that the device be installed approximately 3 hours before starting the actual measurement in order for the device to attain a state of equilibrium.

The results of diligent research by the inventors of the present application, and investigation of the causes of the long-term instability of the analyte extraction amount are described below.

FIG. 1 illustrates the internal structure of a conventional extraction device. An extraction device 1 includes a positive polarity chamber 11, negative polarity chamber 14, positive electrode 12, negative electrode 15, collection materials 13 and 16, and power supply 17. Reference number 18 refers to the skin of a subject, and reference number 20 refers to the internal area of living tissue. The positive polarity chamber 11 and negative polarity chamber 14 are placed on the skin 18. The positive electrode 12 and collection material 13 are accommodated within the positive polarity chamber 11, and the negative electrode 15 and collection material 16 are accommodated in the negative polarity chamber 14. The positive electrode 12 and negative electrode 15 are connected to the power supply 17. The power supply 17 is a constant-current power supply.

When the power supply 17 starts supplying a current, the extraction device 1 forms the electrical circuit shown in FIG. 2. In the drawing, the electrical resistance value of the skin 18 is designated Rep, and the electrical resistance value in the living tissue 20 is designated Rsub.

The condition of the skin 18 after current flow begins via the power supply 17 is described below with reference to FIG. 3, which shows an enlargement of the area 22 of FIG. 2. FIG. 3 illustrates the state of the area 22 after a predetermined time has elapsed following the start of current flow.

An analyte transmission path 24 is formed in the skin 18 via the application of electrical energy from the power supply 17. This analyte transmission path is formed by the enlargement of macropores such as sweat glands, pores and the like, and intercellular micropores via the application of a predetermined energy to the skin, and allows the transmission of analyte within the path. The analyte transmission path is formed more easily with the application of greater energy. The analyte transmission path has a smaller electrical resistance than the other regions of the skin.

The electrical resistance value Rep1 of the analyte transmission path 24 is smaller than the electrical resistance Rep2 of the region outside the analyte transmission path 24 (Rep1<Rep2), and these resistance values are expressed in equation (1) below.

$$1/R_{ep} = 1/R_{ep1} + 1/R_{ep2} \quad (1)$$

When the current flowing through the analyte transmission path 24 is designated Iep1, and the current flowing through the region outside the analyte transmission path 24 is designated Iep2, the equation (2) shown below can be derived.

$$I_{ep1} \times R_{ep1} = I_{ep2} \times R_{ep2} \quad (2)$$

Since the value Rep1 is less than Rep2, the relationship Iep1>Iep2 can be derived from equation (2). That is, although a large current flows in the analyte transmission path 24, a smaller current flows in the region outside the analyte current path. From another perspective, the current is concentrated in the analyte transmission path 24. This means that most of the electrical energy from the power supply 17 is supplied to the analyte transmission path 24, and a lesser amount of electrical energy is supplied to the region in which the analyte transmission path is not yet formed. Accordingly, the analyte transmission path has difficulty forming in the region in which the analyte transmission path is not yet formed, and a long time is required until the path is formed.

When current is flowing continuously after the state shown in FIG. 3 has been attained, the analyte transmission paths are gradually formed even in the region in which the analyte transmission path was not originally formed, and the number of analyte transmission paths becomes constant at a specific time T1 (refer to FIG. 4). The condition of the skin at time T1 is shown in FIG. 5. When at least a predetermined number of analyte transmission paths have been formed, as shown in FIG. 5, the number of analyte transmission paths is stabilized, and a stable amount of analyte can be extracted. However, the conventional extraction device requires a long time (T1) until the analyte transmission paths are formed and the amount of extracted analyte becomes stable because the current is concentrated in only some of the analyte transmission paths.

In view of the above-described circumstances, the present invention provides extraction devices, analyzers, extraction methods and analysis methods which can reduce the waiting time prior to the extraction of the analyte.

SUMMARY

The scope of the present invention is defined solely by the appended claims, and is not affected to any degree by the statements within this summary.

A first extraction device embodying features of the present invention for extracting an analyte from living tissue through skin includes: (a) a first electrode part having a contact area with the skin of less than about 50 mm$^2$; (b) a through-current electrode part; and (c) a power supply part for supplying electrical energy to the first electrode part and the through-current electrode part, and for extracting an analyte in the first electrode part.

A second extraction device embodying features of the present invention for extracting an analyte in living tissue through skin includes: (a) a first path-forming electrode part having a contact area with the skin of less than about 50 mm$^2$; (b) a first extraction electrode part for extracting an analyte; (c) a through-current electrode part; and (d) a power supply part for supplying electrical energy to the first path-forming electrode part, the first extraction electrode part, and the through-current electrode part, for forming analyte transmission paths in the skin for the passage of the analyte, and for extracting the analyte at the first extraction electrode part.

An analyzer embodying features of the present invention for analyzing an analyte extracted through skin includes: (a) an extraction device of a type described above; (b) an assay part for assaying the analyte extracted in the first electrode part, and for outputting a signal corresponding to an amount of the analyte; (c) an analysis part for analyzing the signal output by the assay part to obtain an analysis result; and (d) an output part for outputting the analysis result obtained by the analysis part.

A first extraction method embodying features of the present invention for extracting an analyte in living tissue through skin includes: (a) placing on the skin a through-current electrode part, and a first electrode part having a contact area with the skin of less than about 50 mm$^2$; (b) supplying electrical energy to the through-current electrode part and the first electrode part; and (c) extracting analyte at the first electrode part.

A second extraction method embodying features of the present invention for extracting an analyte in living tissue through skin includes: (a) forming analyte transmission paths in the skin for the passage of analyte; (b) placing a through-current electrode part on the skin; (c) placing a first extraction electrode part on the skin in which the analyte transmission paths are formed; (d) supplying electrical energy to the through-current electrode part and the first extraction electrode part; and (e) extracting analyte at the first extraction electrode part.

A first analysis method embodying features of the present invention for analyzing an analyte extracted through skin includes: (a) extracting an analyte by a method of a type described above; (b) outputting a signal corresponding to an amount of extracted analyte; (c) analyzing the signal to obtain an analysis result; and (d) outputting the analysis result.

A second analysis method embodying features of the present invention for analyzing an analyte extracted through skin includes: (a) extracting an analyte by a method of a type described above; (b) outputting a signal corresponding to an amount of extracted analyte; (c) analyzing the signal to obtain an analysis result; and (d) outputting the analysis result.

DETAILED DESCRIPTION

The extraction devices and methods embodying features of the present invention involve a smaller electrode extraction region and contact area than do conventional extraction devices and methods. Accordingly, it is more difficult for the current to become concentrated in only some of the analyte transmission paths. Therefore, the number of analyte transmission paths becomes stable in a short time after starting the current flow, and the amount of extracted analyte becomes stable in a shorter time. That is, the waiting time before extraction of the analyte is reduced.

The present invention is described hereinafter based on the representative embodiments shown in the accompanying drawings. This description should not be considered to limit the invention in any way.

An extraction device embodying features of the present embodiment employs reverse iontophoresis as the analyte extraction method.

In the present embodiment, an analyte in living tissue is noninvasively extracted through the skin (i.e., percutaneously). Specifically, the method used forms paths for the transmission of analyte in the skin by enlarging macropores such as sweat glands, pores or the like, and intercellular micropores by applying electrical energy to the skin, and extracts analyte through these paths. Skin, in this case, includes the stratum corneum, epidermis, and corium. Tissue below the corium is referred to as living tissue.

The analyte transmission paths are paths formed by the enlargement of macropores such as sweat glands, pores or the like, and intercellular micropores by applying electrical energy to the skin. These paths allow the passage of analyte in the interior of the paths.

Figure 1:
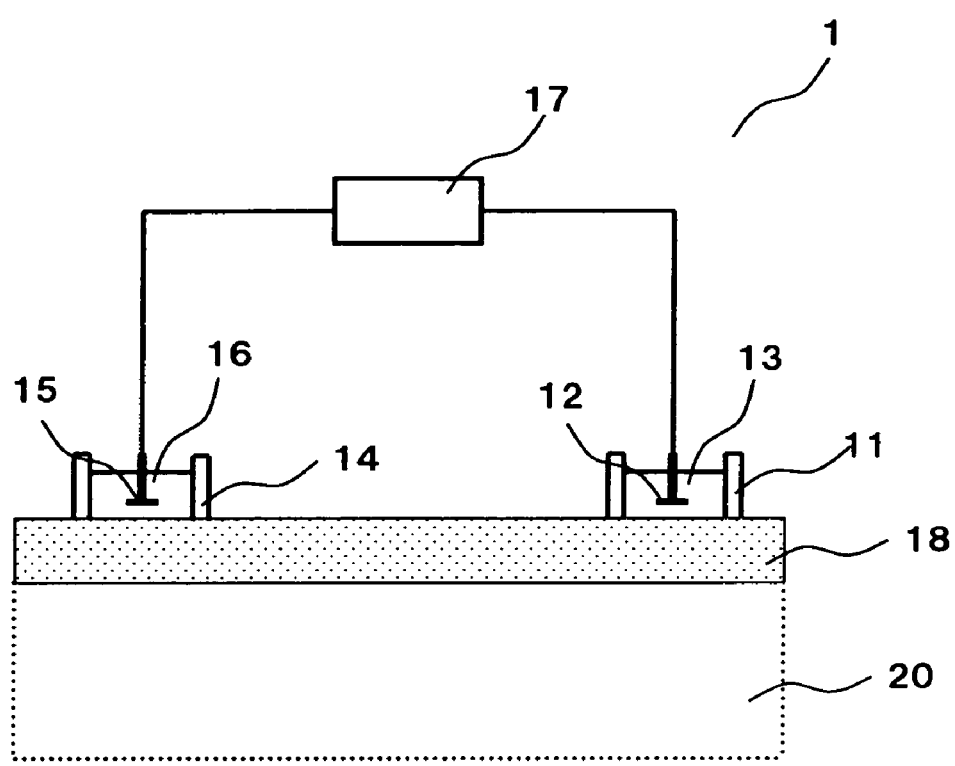
FIG. 1 illustrates the internal structure of a conventional extraction system.
Figure 2:
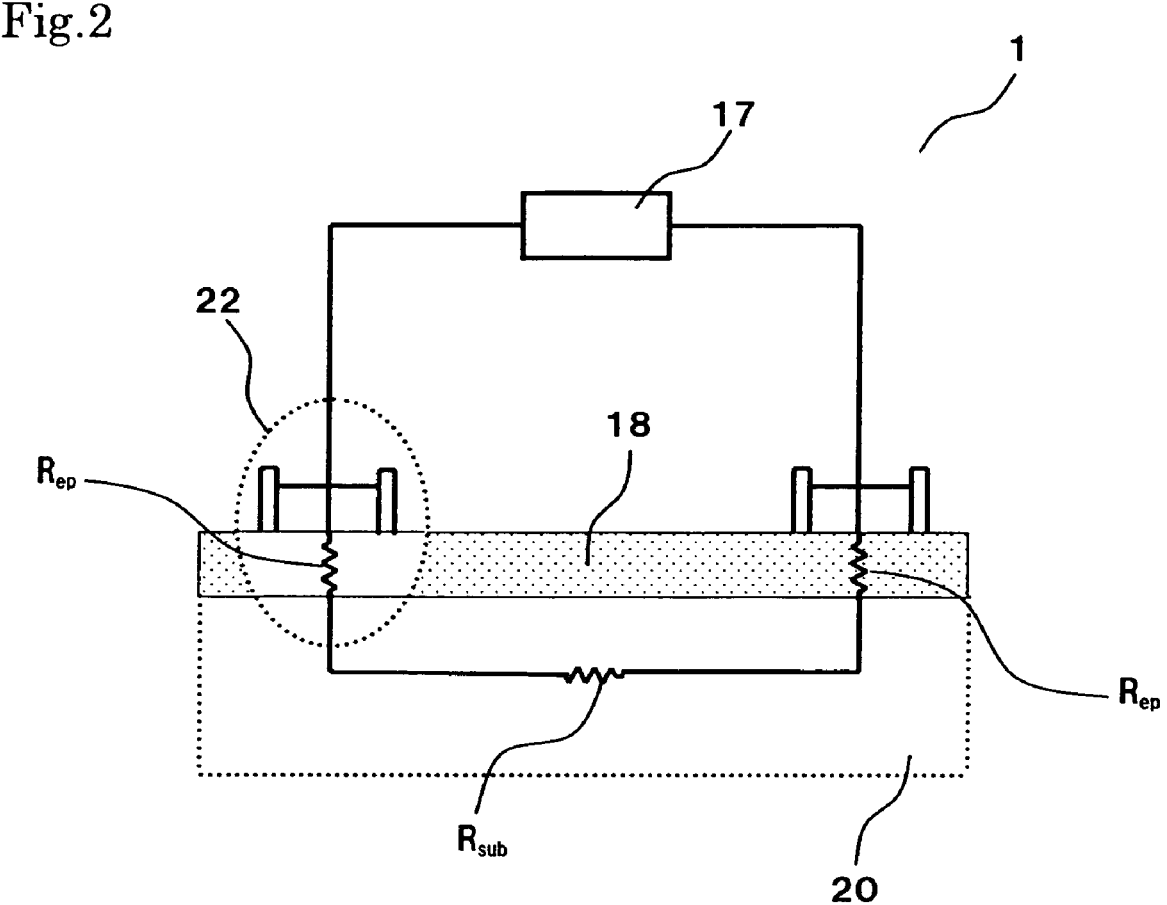
FIG. 2 illustrates the electrical circuit of the extraction system 1.
Figure 3:
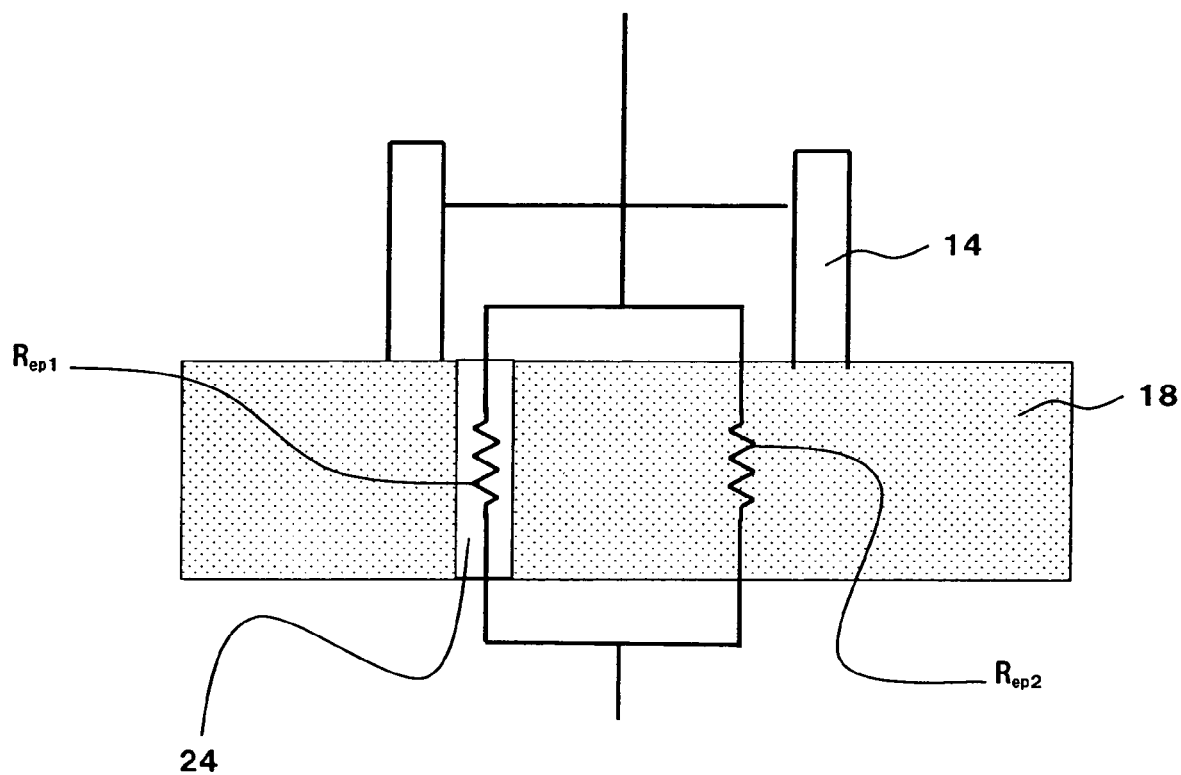
FIG. 3 illustrates the condition of the area 22 after a predetermined time has elapsed since the current flow started.
Figure 4:
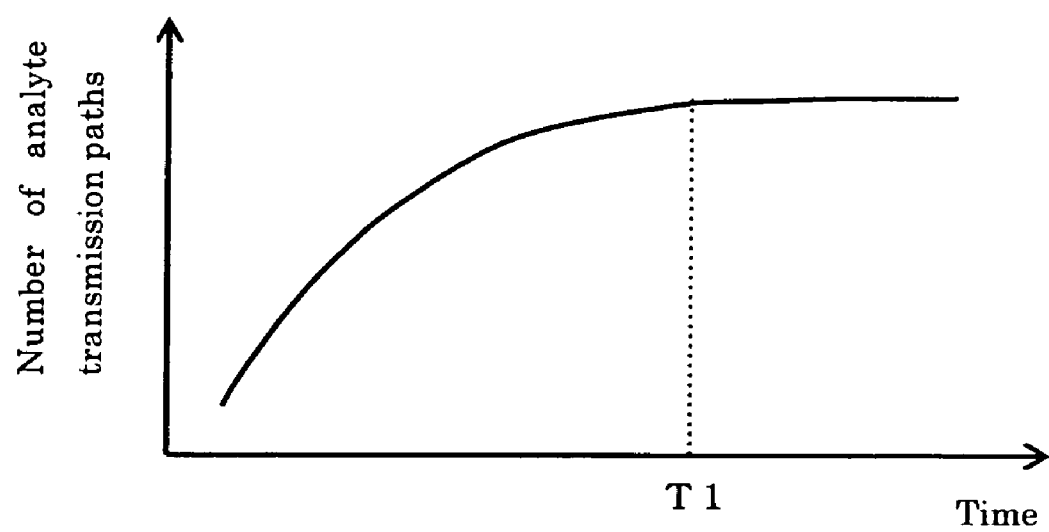
FIG. 4 is a graph showing the relationship between the number of analyte transmission paths and time since the start of current flow.
Figure 5:
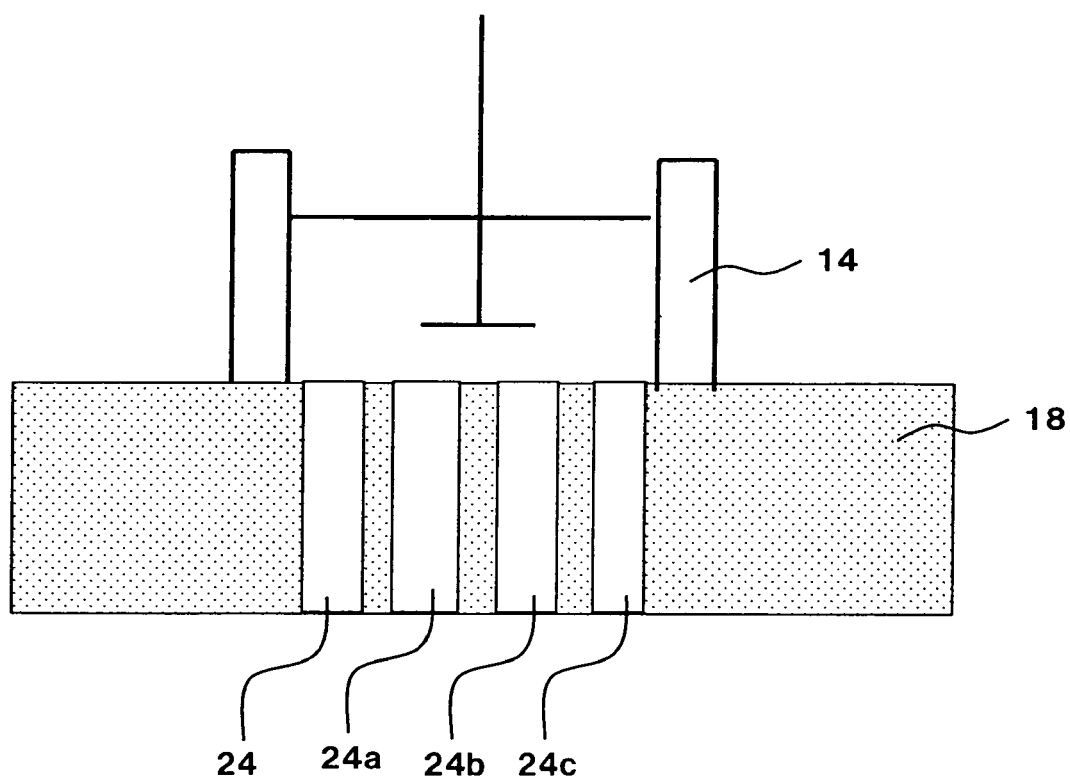
FIG. 5 illustrates the condition of the skin after a time T1 has elapsed since the current flow started.
Figure 6:
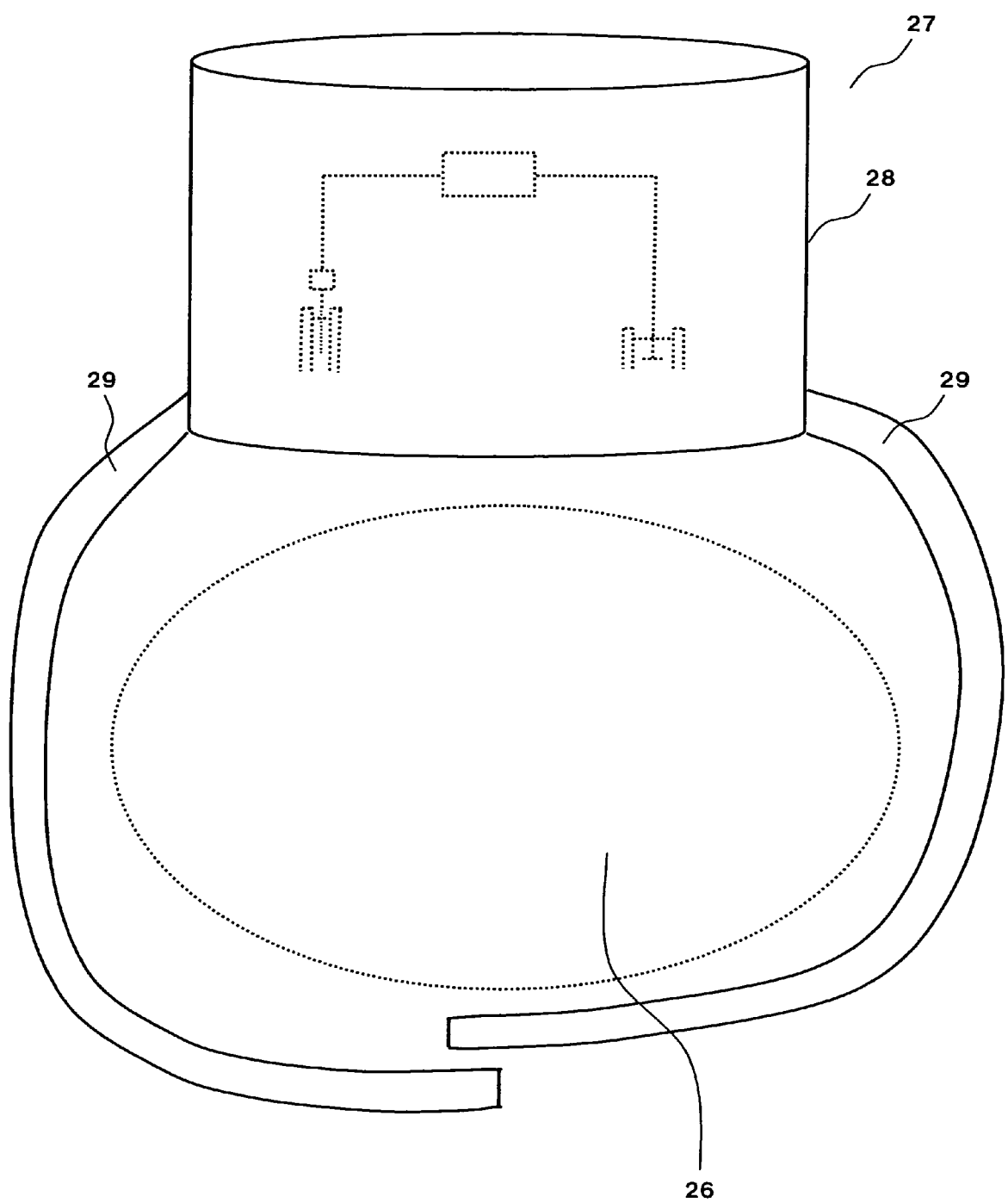
FIG. 6 is an overview of a first extraction device embodying features of the present invention.

FIG. 6 is an overview of a first extraction device embodying features of the present invention.

The extraction device 27 is a device for extracting glucose, and includes a device body 28 and band 29. Reference number 26 indicates the cross section of the wrist of a user.

A user wraps the band 29 on the wrist 26, so as to fix the device body 28 at an optional position on the wrist.

Figure 7:
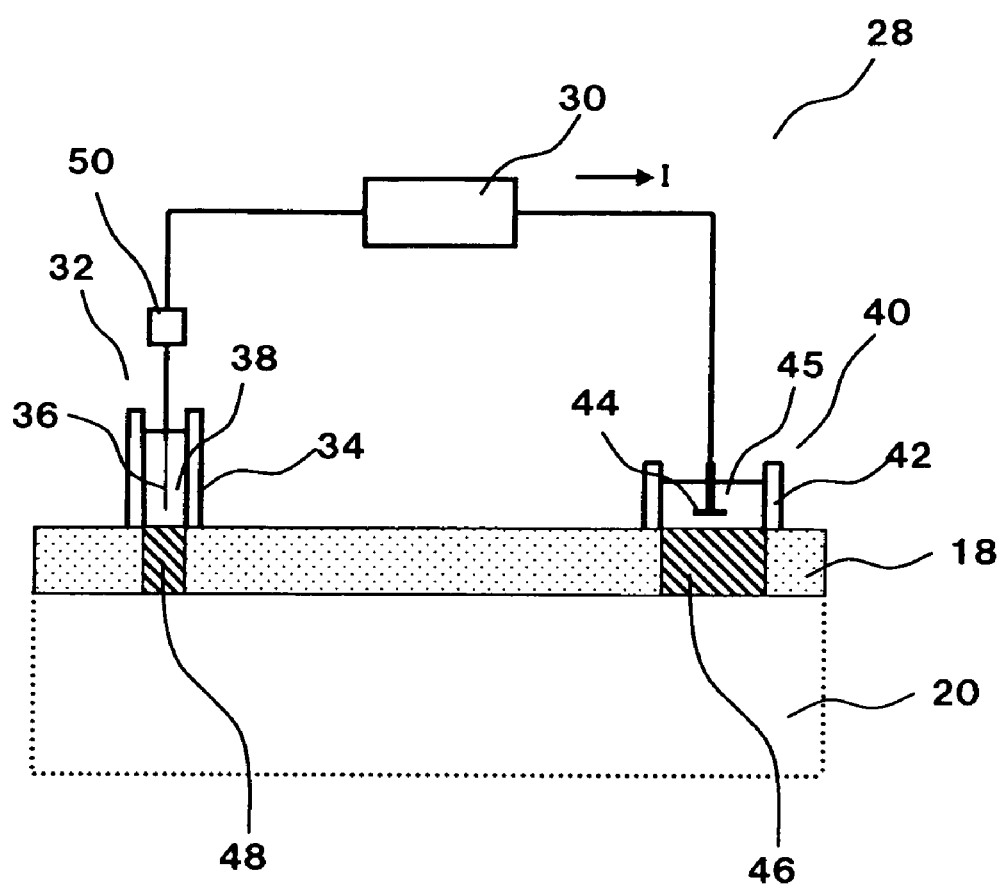
FIG. 7 illustrates the internal structure of the system body 28 when wrapped on a wrist 26.

FIG. 7 illustrates the internal structure of the device body 28 wrapped around a wrist 26. The device body 28 includes a power supply 30 for supplying approximately a 50 µA constant current, a first electrode part 32, a through-current electrode part 40, and a connector 50 for disengaging the power supply 30 and the first electrode part 32.

The first electrode part 32 includes a negative electrode 36 connected to the negative side of the power source 30, a negative electrode chamber 34 within which is arranged the negative electrode 36, and a collection material 38 in contact with the negative electrode 36 accommodated within the negative electrode chamber 34.

The through-current electrode part 40 includes a positive electrode 44 connected to the positive side of the power supply 30, a positive electrode chamber 42 within which is arranged the positive electrode 44, and a collection material 45 in contact with the positive electrode 44 and accommodated in the positive electrode chamber 42.

An AgCl wire is used as the negative electrode 36, ring-shaped Ag wire is used as the positive electrode 44, a glass capillary having an internal diameter of about φ0.6 mm is used as the negative electrode chamber 34, an acrylic chamber having an internal diameter of about φ8 mm is used as the positive electrode chamber 42, and hydroxypropyl cellulose is used as the collection materials 38 and 45.

Since the connector 50 allows the disengagement of the power supply 30 and the first electrode part 32, the first electrode part 32 can be disposable. Thus, reduced accuracy due to contamination can be prevented when assaying the analyte.

The negative electrode 36 and the positive electrode 44 transmit electrical energy to the skin. The negative electrode 36 and the positive electrode 44 may have the same structure, or may have different structures, insofar as the materials used are Ag, AgCl, carbon, platinum or the like.

Although the first electrode part 32 and the through-current electrode part 40 have different structures in the present embodiment, a first electrode part 32 may also be used as the through-current electrode part 40.

The through-current electrode part 40 may also have a configuration so as to be embedded in the skin insofar as it is not painful for the user.

The region of the skin at which the first electrode part 32 is placed is designated the first extraction region 48, and the region of the skin at which the through-current electrode part 40 is placed is designated the positive electrode region 46. The contact area of the first extraction region 48 of the first electrode part 32 is substantially equal to the contact area of the skin and the collection material 38, and since the internal diameter of the negative electrode chamber 34 is about φ0.6 mm, this area is about 0.28 mm$^2$ ($=\pi \times 0.3$ mm$\times 0.3$ mm). The extraction region of the skin is the region of the skin in which analyte transmission paths are formed.

The contact area of the extraction region of the electrode part does not include the surface area of the part of the skin which does not receive the electrical energy application.

Glucose is mainly collected in the first electrode part 32 on the negative electrode side. Accordingly, if the negative side and positive side of the power supply 30 are switched, the glucose is collected mainly in the through-current electrode part 40. For example, if the negative side and positive side of the power supply 30 are switched at predetermined intervals, both the first electrode part 32 and the through-current electrode part 40 can be used for analyte collection. In this case, the through-current electrode part 40 may have the same structure as the first electrode part 32.

The analyte transmission paths may be formed in the first extraction region 48 and the positive electrode region 46.

Figure 8:
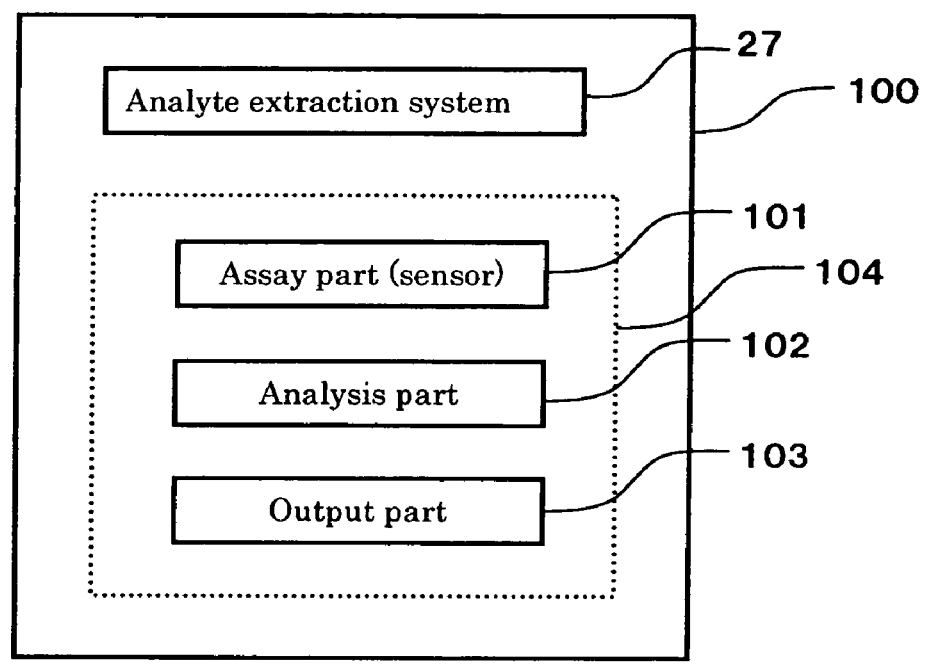
FIG. 8 is a schematic view of the analysis system 100, which includes an extraction system 27.

FIG. 8 is a schematic view of an analyzer 100, which includes the extraction device 27.

The analyzer 100 includes the extraction device 27 and an analysis unit 104. The analysis unit 104 includes an assay part (sensor) 101 for assaying the extracted analyte within the collection material 38 (FIG. 7) and outputting a signal corresponding to the amount of analyte, an analysis part 102 for analyzing the signal output from the assay part 101 and outputting the analysis result, and an output part 103 for outputting (displaying) the analysis result output from the analysis part 102.

The assay part 101 is a sensor which employs an electrochemical detection method using high-performance liquid chromatography (HPLC). A microcomputer including CPU, ROM, RAM, and the like may be used as the analysis part 102, and a liquid crystal display (LCD) may be used as the output part 103.

In addition to the method mentioned above, hexokinase method (HK method), glucose oxidase (GOD) electrode method, glucose oxidase (GOD) colorimetry, and the like may be used as the assay method of the assay part 101. The assay part 101 may be disposable so as to be replaceable for each assay.

A personal computer, server, and the like may also be used as the analysis part 102. A CRT, printer, or communication means connected to another computer also may be used as the output part 103.

Although the extraction device 27 and the analysis unit 104 are separate structures in the present embodiment, the analysis unit 104 also may be integrated within the device body 28.

The method of using the analyzer 100 is described below with reference to the flow chart of FIG. 9, and FIGS. 6-8 and 10.

Figure 9:
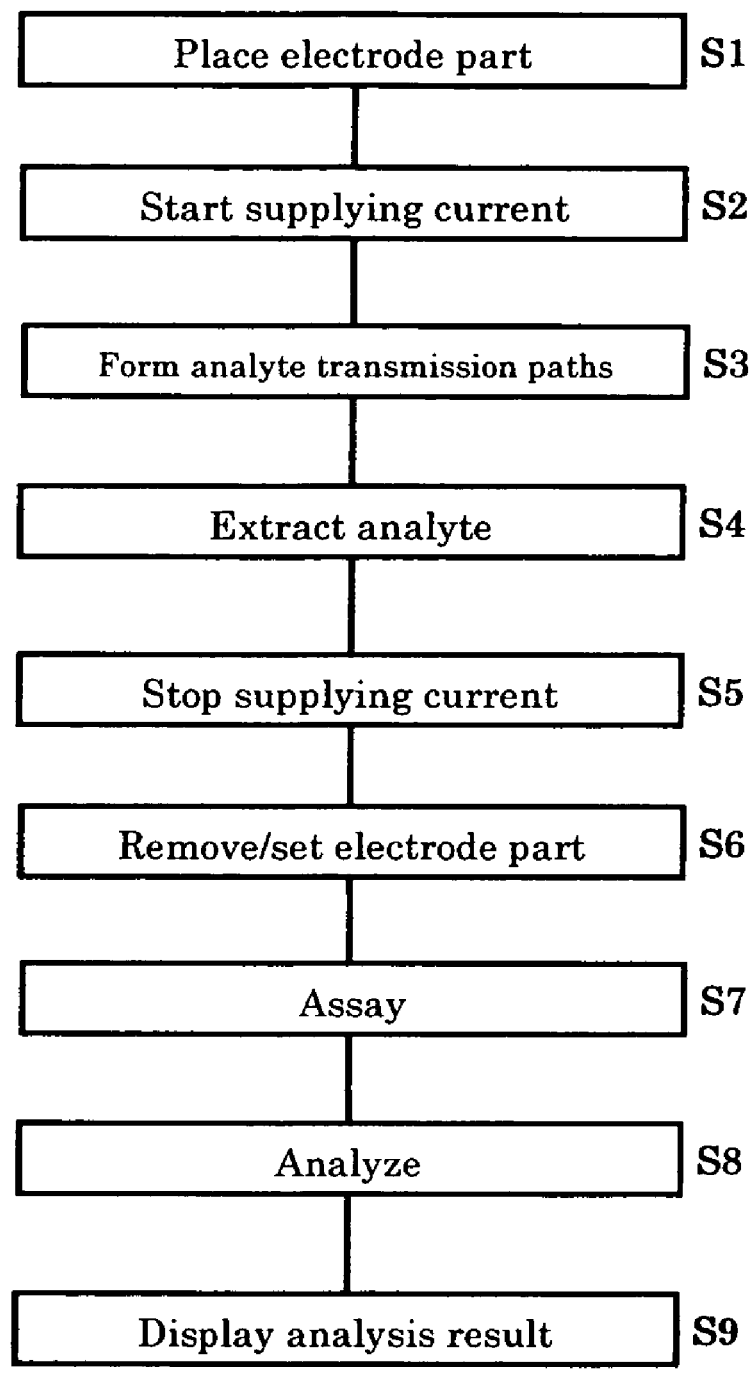
FIG. 9 is a flow chart showing a first method of using the analysis system 100.
Figure 10:
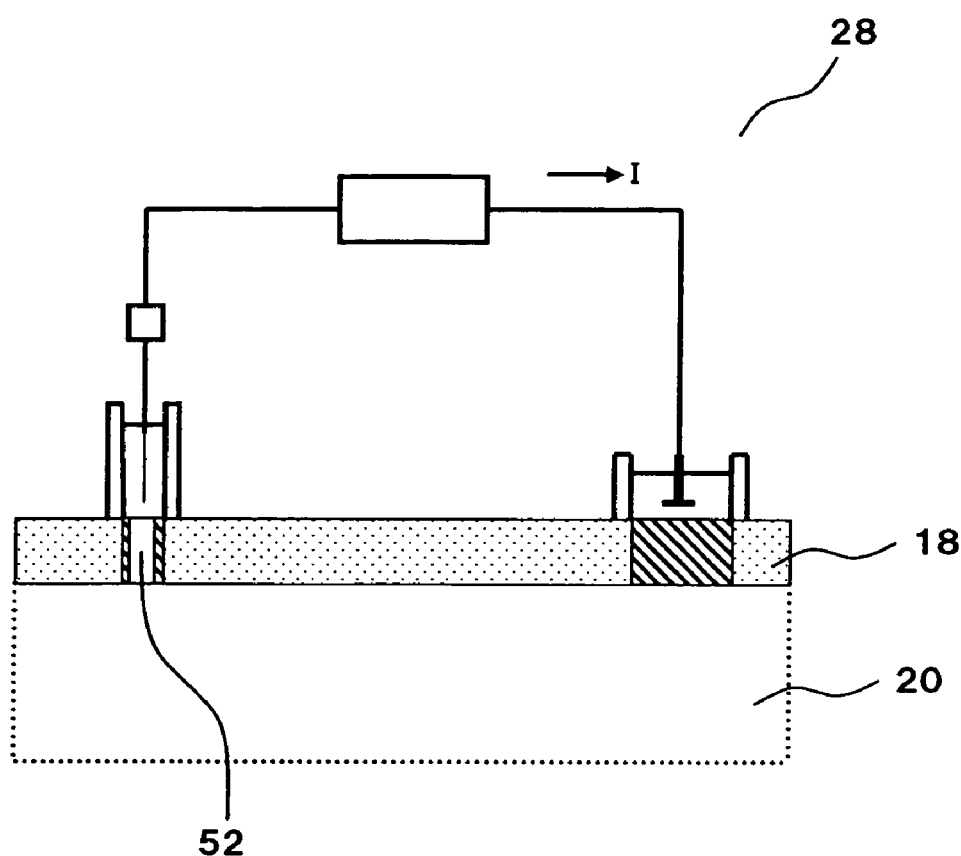
FIG. 10 illustrates the condition of a first region for forming analyte transmission paths.

FIG. 9 is a flow chart illustrating a method of using the analyzer 100. FIG. 10 illustrates the condition of the first region in which analyte transmission paths are formed.

First, the user fixes the first electrode part 32 (FIG. 7) and through-current electrode part 40 on the surface of the skin 18 of the subject by wrapping the band 29 (FIG. 6) around the wrist 26 (S1).

Then, with the positive electrode 44 as the positive electrode side and the negative electrode 36 as the negative electrode side, an approximately 50 µA constant current I is supplied from the power supply 30 (S2).

The current I flows sequentially from the power supply 30 through the through-current electrode part 40, the positive electrode region 46 of the skin, living tissue part 20, first extraction region 48, and the first electrode part 32, and returns to the power supply 30.

Analyte transmission paths 52 (FIG. 10) are formed by the passage of the current through the first extraction region 48 (S3).

Next, analyte is extracted into the collection material 38 through the analyte transmission path 52 via the application of the current I (S4).

The analyte extraction is stopped by stopping the application of the current I (S5).

The user disconnects the connector 50 and removes the first electrode part 32 from the first extraction region 48, and sets the first electrode part 32 in the assay part 101 of the analysis unit 104 (FIG. 8) (S6).

A signal corresponding to the amount of extracted analyte (glucose) in the first electrode part 32 is output to the analysis part 102 by the assay part 101 (S7).

The signal output from the assay part 101 is analyzed by the analysis part 102, and the analysis result is output to the output part 103 (S8).

The analysis result output from the analysis part 102 is displayed by the output part 103 (S9).

Another method of using the analyzer 100 is described below with reference to the flow chart of FIG. 11 and FIGS. 6-8 and 10.

Figure 11:
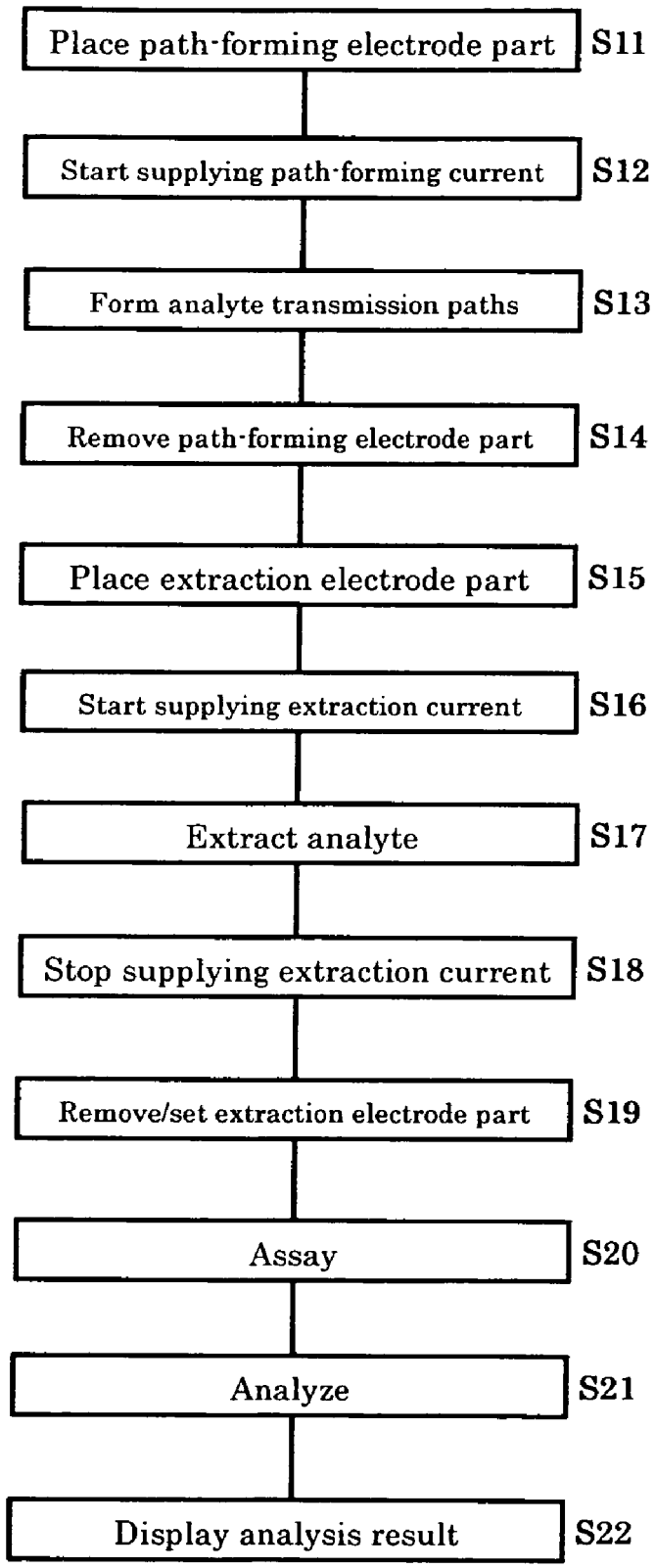
FIG. 11 is a flow chart showing a second method of using the analysis system 100.

FIG. 11 is a flow chart illustrating another method of using the analyzer 100.

First, the user places the first electrode part 32 (FIG. 7) and through-current electrode part 40 on the surface of the skin 18 of the subject by wrapping the band 29 (FIG. 6) around the wrist 26 (S11). The first electrode part 32 is the path-forming electrode part used to form the analyte transmission paths in the first extraction region 48.

Then, with the positive electrode 44 as the positive electrode side and the negative electrode 36 as the negative electrode side, an approximately 50 μA constant current I is supplied from the power supply 30 (S12).

The current I flows sequentially from the power supply 30 through the through-current electrode part 40, the positive electrode region 46 of the skin, living tissue part 20, first extraction region 48, and the first electrode part 32, and returns to the power supply 30.

Analyte transmission paths 52 (FIG. 10) are formed by the passage of the current through the first extraction region 48 (S13).

The current I is stopped, connector 50 is removed, and the first electrode part 32 is removed from the first extraction region 48 (S14).

Next, another first electrode 32 is connected to the connector 50, and this first electrode part 32 is placed on the first extraction region 48 (S15). This new first electrode part 32 is used as the extraction electrode part for extracting analyte through the analyte transmission paths.

Then, with the positive electrode 44 as the positive electrode side and the negative electrode 36 as the negative electrode side, an approximately 50 μA constant current I is supplied from the power supply 30 (S16).

Analyte is extracted into the collection material 38 through the analyte transmission path 52 via the application of the current I (S17).

The analyte extraction is stopped by stopping the application of the current I (S18).

The user disconnects the connector 50 and removes the first electrode part 32 from the first extraction region 48, and sets the first electrode part 32 in the assay part 101 of the analysis unit 104 (FIG. 8) (S19).

A signal corresponding to the amount of extracted analyte (glucose) in the first electrode part 32 is output to the analysis part 102 by the assay part 101 (S20).

The signal output from the assay part 101 is analyzed by the analysis part 102, and the analysis result is output to the output part 103 (S21).

The analysis result output from the analysis part 102 is displayed by the output part 103 (S22).

Although the first electrode part 32 is used as the path-forming electrode part and the extraction electrode part in the present embodiment, electrode parts having respectively separate structures also may be used.

Although currents having identical magnitude and direction are used as the current I in S13 and S17, these magnitudes and directions also may be mutually different.

The extraction device 27 also may be constructed so as to allow the analyte transmission path-forming electrode part and the extraction electrode part to be connected at the same time.

Another embodiment in accordance with the present invention is described below.

Figure 12:
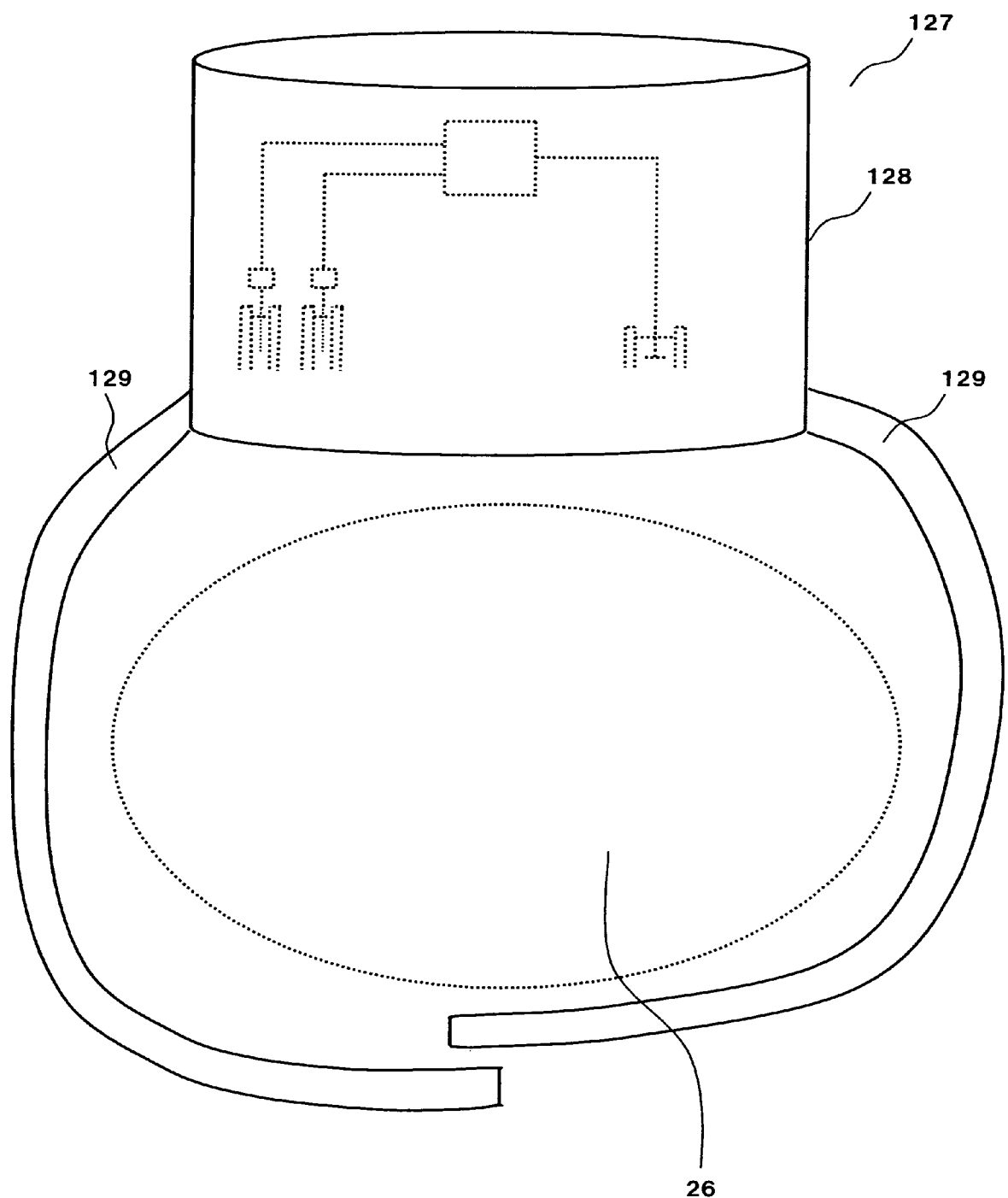
FIG. 12 is an overview of a second extraction system embodying features of the present invention.

FIG. 12 is a perspective view of a second extraction device embodying features of the present invention.

The extraction device 127 is a device for extracting glucose, and includes a body 128 and band 129. Reference number 26 indicates the cross section of the wrist of a user.

A user wraps the band 129 on the wrist 26, so as to fix the device body 128 at an optional position on the wrist.

Figure 13:
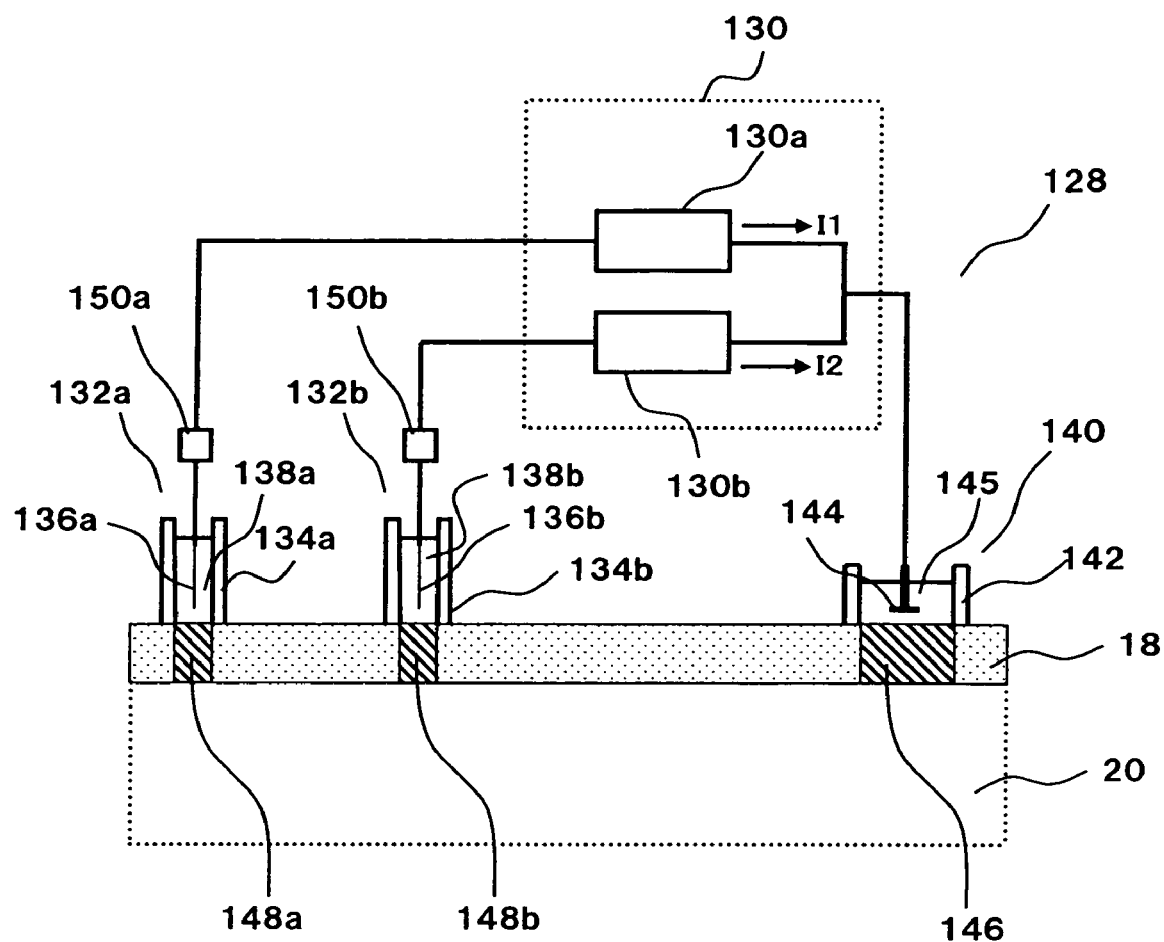
FIG. 13 illustrates the internal structure of the system body 128 when wrapped on a wrist 26.

FIG. 13 illustrates the internal structure of the device body 128 wrapped around a wrist 26. The device body 128 includes a power supply part 130, a first electrode part 132a, a second electrode part 132b, a through-current electrode part 140, a connector 150a for disengaging the first power supply 130a and the first electrode part 132a, and a connector 150b for disengaging the second power supply 130b and second electrode part 132b.

The power supply part 130 includes a first power supply 130a for supplying an approximately 50 μA constant current, and a power supply 130b for supplying an approximately 50 μA constant current.

The first electrode part 132a includes a negative electrode 136a connected to the negative side of the first power supply 130a, a negative electrode chamber 134a within which is arranged the negative electrode 136a, and a collection material 138a in contact with the negative electrode 136a and accommodated in the negative electrode chamber 134a.

The second electrode part 132b includes a negative electrode 136b connected to the negative side of the second power supply 130b, a negative electrode chamber 134b within which is arranged the negative electrode 136b, and a collection material 138b in contact with the negative electrode 136b and accommodated in the negative electrode chamber 134b.

Although the first electrode part 132a and the second electrode part 132b have the same structure in the present embodiment, their structures also may be different.

The through-current electrode part 140 includes a positive electrode 144 connected to the positive side of both the first power supply 130a and the second power supply 130b, a positive electrode chamber 142 within which is arranged the positive electrode 144, and a collection material 145 in contact with the positive electrode 144 and accommodated within the positive electrode chamber 142.

Silver chloride (AgCl) wires are used as the negative electrodes 136a and 136b, a ring-shaped Ag wire is used as the positive electrode 144, glass capillaries having an internal diameter of about ϕ0.6 mm are used as the negative electrode chambers 134a and 134b, an acrylic chamber having an internal diameter of about ϕ8 mm is used as the positive electrode chamber 142, and hydroxypropyl cellulose is used as the collection materials 138a, 138b, and 145.

The same material, or different materials, may be used as the collection materials 138a, 138b, and 145.

The collection materials 138a and 138b may be integratedly formed insofar as they are mutually insulated one from another.

Although the first electrode part 132a, the second electrode part 132b, and the through-current electrode part 140 have different structures in the present embodiment, either first electrode part 132a or 132b may be used as the through-current electrode part 140.

A first through-current electrode part connected to the first power supply 130a, and a second through-current electrode part connected to the second power supply 130b may be used in place of the through-current electrode part 140.

The region of the skin on which the first electrode part 132a is placed is the first extraction region 148a, the region of the skin on which the second electrode part 132b is placed is the second extraction region 148b, and the region of the skin on which the through-current electrode part 140 is placed is the positive electrode region 146.

The second extraction region 148b is the region of the skin in which the analyte transmission paths are formed by the second electrode 132b, and is a different region than the first extraction region 148a. The contact area of the first extraction region 148a of the first electrode part 132a is equal to the contact area of the skin and the collection material 138a, and since the internal diameter of the negative electrode chamber 134a is about φ0.6 mm, this area is about 0.28 mm$^2$ (=π×0.3 mm×0.3 mm). Similarly, the contact area of the second extraction region 148b of the second electrode part 132b is substantially equal to the contact area of the skin and the collection material 138b, and since the internal diameter of the negative electrode chamber 134b is about φ0.6 mm, this area is about 0.28 mm$^2$ (=π×0.3 mm×0.3 mm).

In accordance with this second extraction device embodying features of the present invention, since the total contact area of the extraction regions of the extraction electrode parts is larger than that of the extraction device of the first embodiment, the amount of extracted analyte can be increased. Accordingly, the accuracy is improved when assaying the analyte.

Glucose is mainly collected in the first electrode part 132a and second electrode part 132b on the negative electrode side. Accordingly, if the negative side and positive side of the first power supply 130a and the second power supply 130b are switched, the glucose is collected mainly in the through-current electrode part 140. For example, if the negative side and positive side of the first power supply 130a and the second power supply 130b are switched at predetermined intervals, both the first electrode part 132a and the second electrode part 132b, and the through-current electrode part 140 can be used for analyte collection. In this case, the through-current electrode part 140 may have the same construction as the first electrode part 132a or the second electrode part 132b.

The analyte transmission paths may be formed in the first extraction region 148a, the second extraction region 148b, and the positive electrode region 146.

Figure 14:
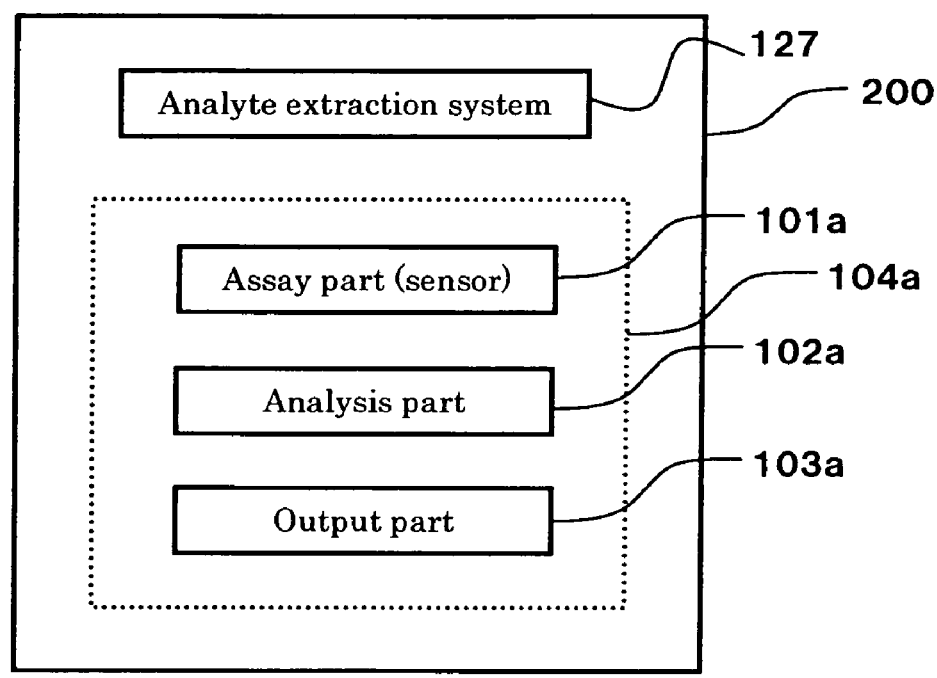
FIG. 14 is a schematic view showing an analysis system 200, which includes an extraction system 127.

FIG. 14 is a schematic view of an analyzer 200, which includes the extraction device 127.

The analyzer 200 includes the extraction device 127 and an analysis unit 104a. The analysis unit 104a includes an assay part (sensor) 101a for assaying the extracted analyte within the collection materials 138a and 138b (FIG. 13) and outputting a signal corresponding to the amount of analyte, an analysis part 102a for analyzing the signal output from the assay part 101a and outputting the analysis result, and an output part 103a for outputting (displaying) the analysis result output from the analysis part 102a.

The assay part 101a is a sensor which employs an electrochemical detection method using high-performance liquid chromatography (HPLC). A microcomputer including CPU, ROM, RAM, and the like may be used as the analysis part 102a, and a liquid crystal display (LCD) may be used as the output part 103a.

Although the extraction device 127 and the analysis unit 104a have separate structures in the present embodiment, the analysis unit 104a may be integrated within the device body 128.

The method of using the analyzer 200 is described below with reference to the flow chart of FIG. 15, and FIGS. 12-14 and 16.

Figure 15:
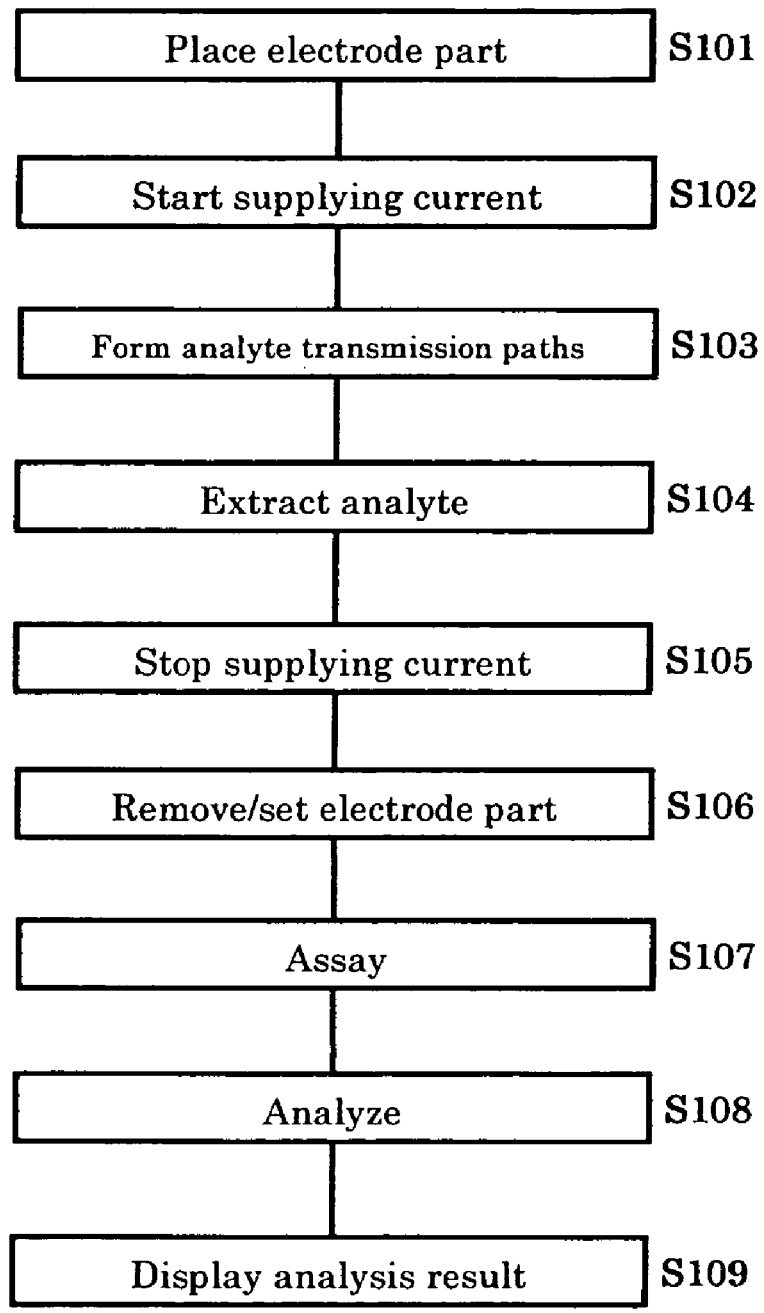
FIG. 15 is a flow chart showing a first method of using the analysis system 200.
Figure 16:
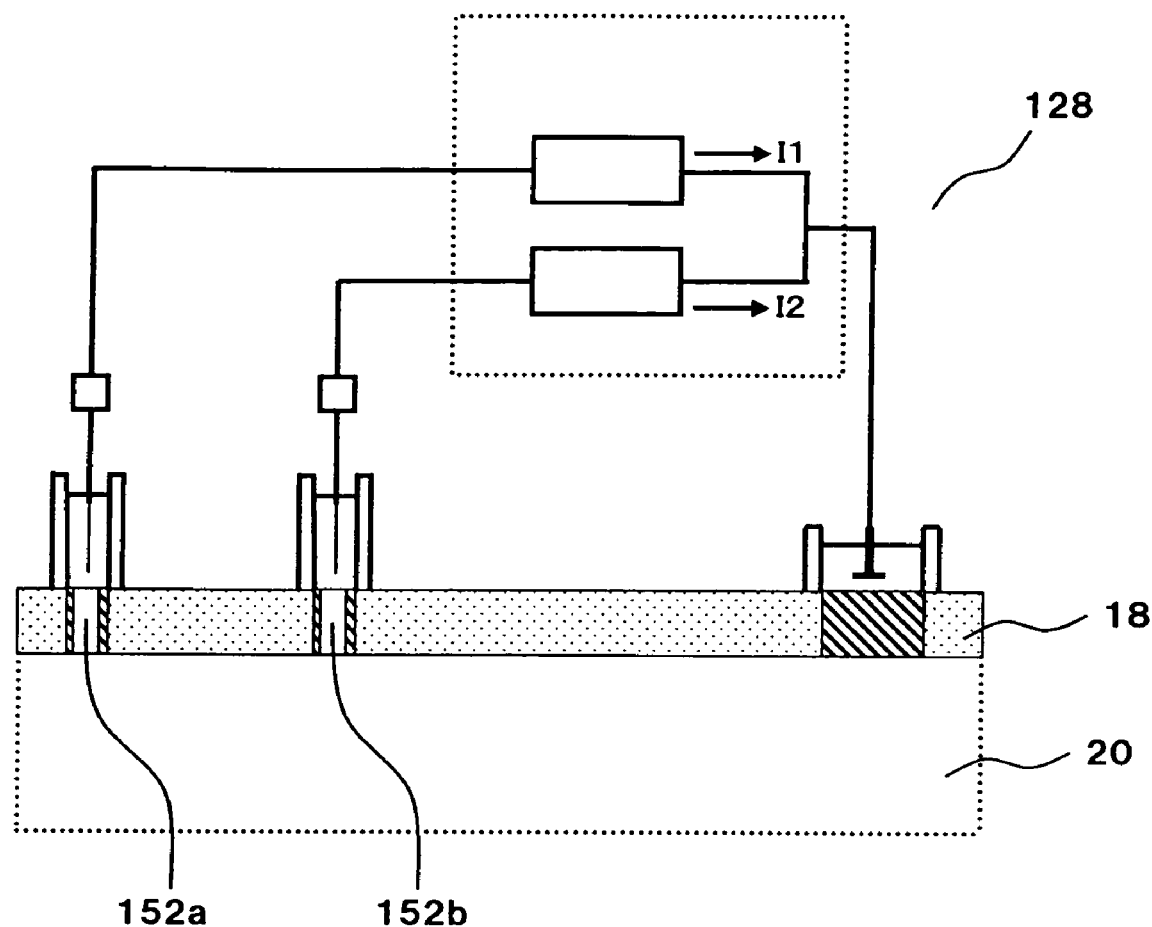
FIG. 16 illustrates the condition of a first region and a second region for forming analyte transmission paths.

FIG. 15 is a flow chart illustrating a method of using the analyzer 200. FIG. 16 illustrates the condition of the first region and the second region in which analyte transmission paths are formed.

First, the user fixes the first electrode part 132a (FIG. 13), second electrode part 132b, and through-current electrode part 140 on the surface of the skin 18 of the subject by wrapping the band 129 (FIG. 12) around the wrist 26 (S101).

Then, with the positive electrode 144 as the positive electrode side and the negative electrodes 136a and 136b as the negative electrode side, approximately 50 μA constant currents I1 and I2 are respectively supplied from the first power supply 130a and the second power supply 130b (S102).

At least part of the current I1 flows sequentially from the first power supply 130a through the through-current electrode part 140, the positive electrode region 146 of the skin, living tissue part 20, first extraction region 148a, and the first electrode part 132a, and returns to the first power supply 130a.

At least part of the current I2 flows sequentially from the second power supply 130b through the through-current electrode part 140, the positive electrode region 146 of the skin, living tissue part 20, second extraction region 148b, and the second electrode part 132b, and returns to the second power supply 130b.

The analyte transmission paths 152a and 152b (FIG. 16) are formed by the current passing through the first extraction region 148a and the second extraction region 148b (S103).

Then, the analyte passing through the analyte transmission paths 152a and 152b is extracted into the collection materials 138a and 138b by the application of the currents I1 and I2 (S104).

The extraction of the analyte ends when the currents I1 and I2 stop (S105).

The user removes the connectors 150a and 150b, and removes the first electrode part 132a and the second electrode part 132b from the first extraction region 148a and second extraction region 148b. The first electrode part 132a and the second electrode part 132b are set in the assay part 101a of the analysis unit 104a (FIG. 14) (S106).

A signal corresponding to the amount of analyte (glucose) extracted in the first electrode part 132a and the second electrode part 132b is output to the analysis part 102a by the assay part 101a (S107).

The signal output from the assay part 101a is analyzed by the analysis part 102a, and the analysis result is output to the output part 103a (S108).

The analysis result output from the analysis part 102a is displayed by the output part 103a (S109).

The placement of the first electrode part 132a and the second electrode part 132b on the skin in S101 may occur simultaneously or with shifted timing.

The application of the current I1 and the application of the constant current I2 in S102 may occur simultaneously or with shifted timing.

Another method of using the analyzer 200 is described below with reference to the flow chart of FIG. 17, and FIGS. 12-14, and 16.

Figure 17:
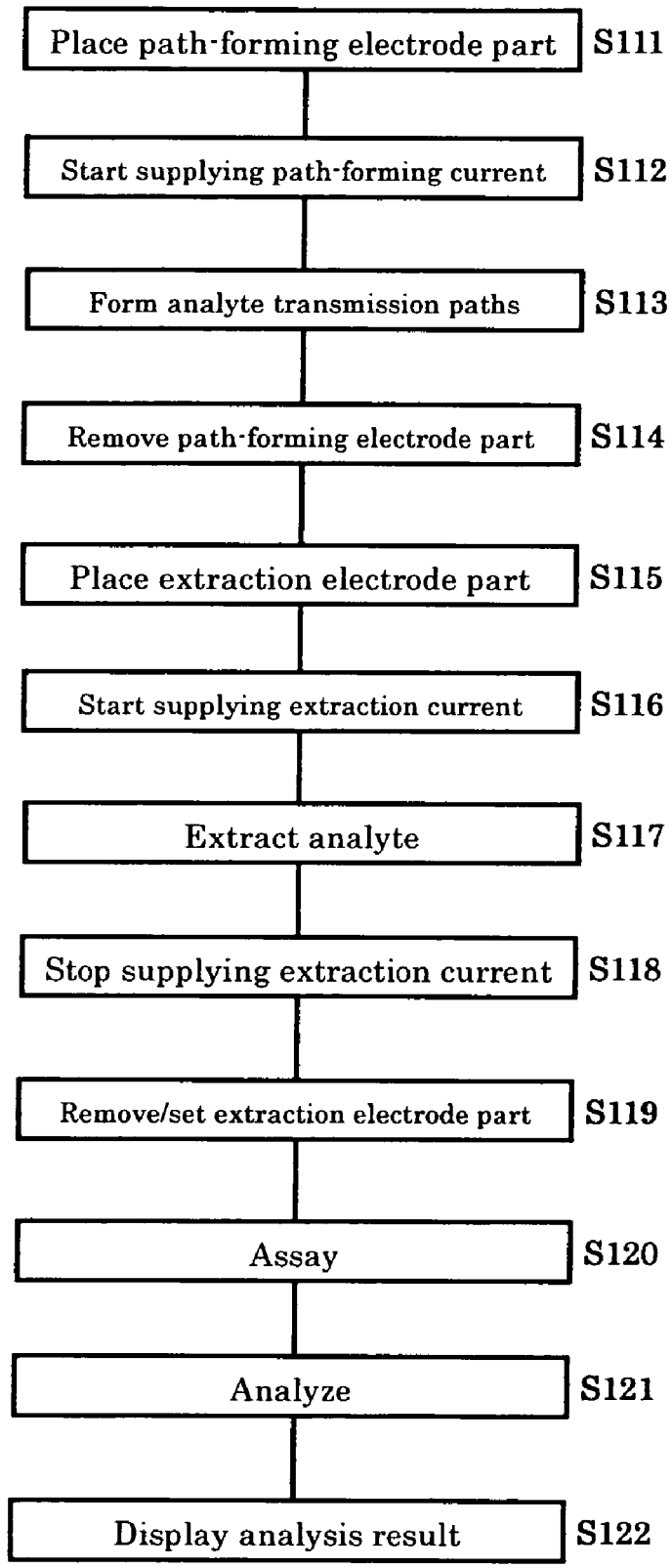
FIG. 17 is a flow chart showing a second method of using the analysis system 200.

FIG. 17 is a flow chart illustrating another method of using the analyzer 200.

First, the user places the first electrode part 132a (FIG. 13), the second electrode part 132b, and the through-current electrode part 140 on the surface of the skin 18 of the subject by wrapping the band 129 (FIG. 12) around the wrist 26 (S111). The first electrode part 132a and the second electrode part 132b are the path-forming electrode parts used to form the analyte transmission paths in the first extraction region 148a and the second extraction region 148b.

Then, with the positive electrode 144 as the positive electrode side and the negative electrodes 136a and 136b as the negative electrode side, approximately 50 μA constant currents I1 and I2 are supplied from the first power supply 130a and the second power supply 130b (S112).

At least part of the current I1 flows sequentially from the first power supply 130a through the through-current electrode part 140, the positive electrode region 146 of the skin, living tissue part 20, first extraction region 148a, and the first electrode part 132a, and returns to the first power supply 130a.

At least part of the current I2 flows sequentially from the second power supply 130b through the through-current electrode part 140, the positive electrode region 146 of the skin, living tissue part 20, second extraction region 148b, and the second electrode part 132b, and returns to the second power supply 130b.

The analyte transmission paths 152a and 152b (FIG. 16) are formed by the current passing through the first extraction region 148a and the second extraction region 148b (S113).

The currents I1 and I2 are stopped, connectors 150a and 150b are removed, and the first electrode part 132a and the second electrode part 132b are removed from the first extraction region 148a and the second extraction region 148b (S114).

Next, another first electrode part 132a and second electrode part 132b are respectively connected to the connectors 150a and 150b, and the first electrode part 132a and the second electrode part 132b are respectively placed on the first extraction region 148a and the second extraction region 148b (S115). The new first electrode part 132a and the second electrode part 132b are extraction electrode parts used for extracting analyte through the analyte transmission paths.

Then, with the positive electrode 144 as the positive electrode side and the negative electrodes 136a and 136b as the negative electrode side, approximately 50 μA constant currents I1 and I2 are respectively supplied from the first power supply 130a and the second power supply 130b (S116).

Then, the analyte is extracted into the collection materials 138a and 138b by the application of the current flowing through the analyte transmission paths 152a and 152b (S117).

The extraction of the analyte ends when the currents I1 and I2 stop (S118).

The user removes the connectors 150a and 150b, removes the first electrode part 132a and the second electrode part 132b from the first extraction region 148a and the second extraction region 148b, and the first electrode part 132a and the second electrode part 132b are set in the assay part 101a of the analysis unit 104a (S119).

A signal corresponding to the amount of analyte (glucose) extracted in the first electrode part 132a and the second electrode part 132b is output to the analysis part 102a by the assay part 101a (FIG. 14) (S120).

The signal output from the assay part 101a is analyzed by the analysis part 102a, and the analysis result is output to the output part 103a (S121).

The analysis result output from the analysis part 102a is displayed by the output part 103a (S122).

Although the first electrode part 132a and the second electrode part 132b are used as the path-forming electrodes in the present embodiment, electrode parts having separate structures also may be used as the path-forming electrode part and extraction electrode part.

Although currents having substantially identical magnitude and direction are used as the current I1 in S113 and S117, these magnitudes and directions also may be mutually different. The same is true for the current I2.

Although the application of the constant current I1 and the application of the constant current I2 occur substantially simultaneously in S112, the timing of these applications may be shifted. Similarly, the timing of the removal of the electrode parts and the current applications in S114 and S116 also may be shifted.

Although two electrode parts 132a and 132b (FIG. 13) are used as the path-forming electrode part or extraction electrode part in the present embodiment, the invention is not limited to this configuration, inasmuch as three or more electrode parts may also be used. In this case, the electrode parts may be integrated. Moreover, the number of power supplies 130a and 130b and the like may be equal to or greater than the number of electrode parts.

Figure 18:
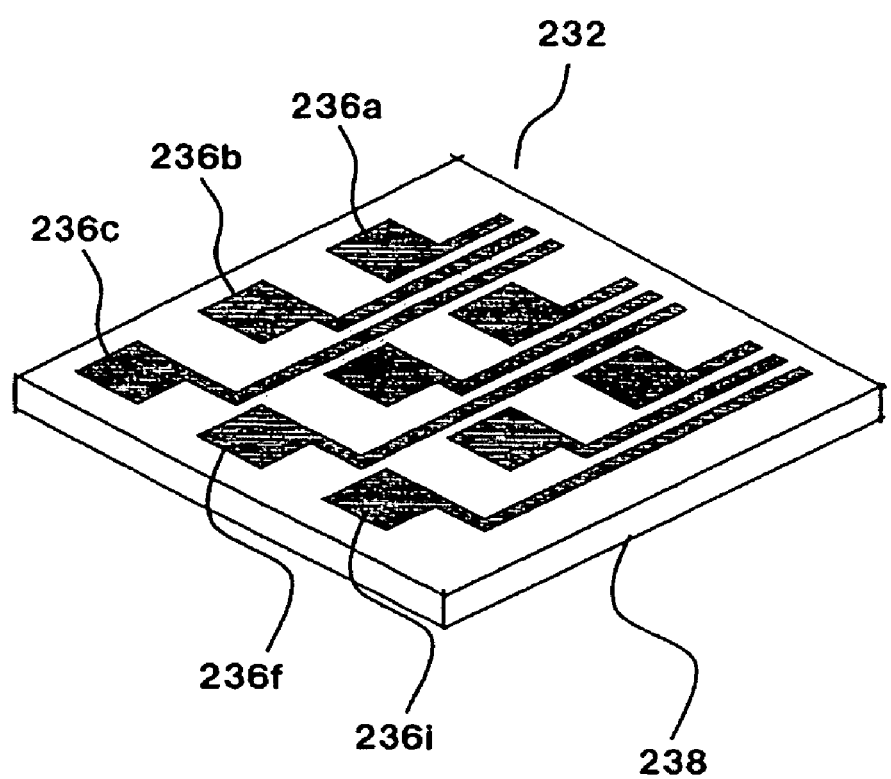
FIG. 18 is a perspective view of a path-forming electrode part 232.

FIG. 18 shows an embodiment in accordance with the present invention having an integrated path-forming electrode part. The path-forming electrode part 232 includes a rectangular collection material 238, and nine electrodes 236a, 236b, 236c, . . . 236f, . . . 236i adhered in rows on the top surface of the collection material 238, such that the respective electrodes are detachably connected to the power supplies 130a, 130b and the like (FIG. 13). Silver chloride (AgCl) is used as the electrodes 236a and the like, and hydroxypropyl cellulose is used as the collection material 238. One electrode and the collection material 238 directly below the electrode may be integratedly formed as a single electrode part. That is, the path-forming electrode part 232 may have a structure of nine integrated electrode parts.

The bottom surface of the collection material 238 is square in shape with a side of about 9 mm. Accordingly, the contact area of the collection material 238 and the skin is about 81 mm$^2$ (=9×9 mm). Since there are nine electrode parts, the contact area of each electrode part and the extraction region of the skin is about 9 mm$^2$ (=81 mm2÷9).

The path-forming electrode part 232 may also be used as the extraction electrode part.

When the path-forming electrode part 232 is used to form the analyte transmission paths, a part having a total contact area of the electrodes parts and the skin exceeding about 50 mm$^2$, as in the through-current electrode part 140, may be used as the extraction electrode part.

When a plurality of path-forming electrode parts are used, the total contact area of the path-forming electrode parts and the extraction regions of the skin is desirably between about 0.1 and about 200 mm$^2$, and more desirably between about 1 and about 50 mm$^2$.

Similarly, when a plurality of extraction electrode parts are used, the total contact area of the extraction electrode parts and the extraction regions of the skin is desirably between about 0.1 and about 200 mm², and more desirably between about 1 and about 50 mm².

Although the extraction devices of the above described embodiments use reverse iontophoresis, the present invention is not limited to this method, inasmuch as other methods may be used. For example, sonophoresis methods, which extract analyte in living tissue by irradiating the extraction region of the skin by ultrasonic waves to reduce the barrier function of the skin and promote passive diffusion, may be used. In addition, negative pressure suction methods, which extract analyte in living tissue by suctioning the extraction region of the skin under negative pressure, may be used. Furthermore, chemical enhancer methods, which administer a drug to promote percutaneous migration of analyte in the extraction region of the skin, and the like may be used in suitable combinations.

For example, the extraction devices 27 and 127 described above also may be provided with an ultrasonic irradiation part for irradiating the extraction region with ultrasonic waves, a suction part for suctioning the extraction region under negative pressure, and a drug administration part for administering a drug to the extraction region.

Menthol, alcohol, surface active agents, and the like may be used as drugs for promoting percutaneous migration of the analyte.

In this way, the amount of extracted analyte can be increased, and greater analysis accuracy is possible.

Furthermore, these methods may be used not only to extract analyte, but also for promoting the formation of the analyte transmission paths.

When the contact area of the electrode part and the extraction region of the skin exceeds about 50 mm², the current becomes concentrated in part of the analyte transmission path, such that a long time is required until a predetermined number of analyte transmission paths are formed, and the waiting time is increased before analyte can be extracted.

Conversely, when the contact area of the electrode part and extraction region of the skin is less than about 0.01 mm², a long time is required to extract the amount of analyte necessary for analysis.

Even when the contact area is less than about 0.01 mm², the detection sensitivity of the assay part (sensor) is increased, such that the time required for extraction can be reduced by using a combination of other analyte extraction methods.

From this perspective, the contact area of the electrode part and the extraction region may be between about 0.01 and about 50 mm².

From the standpoint of reducing the waiting time before extracting the analyte, the contact area of the electrode part and the extraction region is desirably between about 0.01 and about 25 mm². From the perspective of reducing the waiting time, the contact area of the electrode part and the extraction region may also be between about 0.01 and about 10 mm², between about 0.01 and about 5 mm², and between about 0.01 and about 1 mm².

Furthermore, from the standpoint of ensuring the amount of extracted analyte, the contact area of the electrode part and the extraction region may also be between about 0.1 and about 50 mm², and between about 0.5 and about 50 mm².

Accordingly, from the perspective of reducing the waiting time and ensuring the extraction amount, the contact area of the electrode part and the extraction region may also be between about 0.1 and about 25 mm², between about 0.1 and about 10 mm², and between about 0.1 and about 5 mm².

The magnitude of the current supplied from the power supply is desirably less than about 300 μA. This magnitude produces minimal discomfort to the user of the extraction device. It is desirable that the magnitude of the current is between about 10 and about 300 μA. This magnitude allows the formation of analyte transmission paths and the extraction of analyte in a short time, and produces minimal discomfort for the user of the extraction device.

Purified water, ion-conductive aqueous solution (e.g., physiological saline solution), hydrogel, ion-conductive hydrogel, and the like may be used as the collection material. Examples of ion-conductive hydrogels include but are not limited to polyacryate, polyvinyl alcohol, hydroxypropyl cellulose, and the like.

A direct current power supply, alternating current power supply, and a combination of direct current power supply and alternating current power supply may be used as the power source. From the perspective of stabilizing the amount of extracted analyte, a constant-current power supply or a constant-voltage power supply is desirable to use as the power supply.

When a constant-voltage power supply is used as the power source, the voltage output by the power supply should be capable of extracting the required amount of analyte for analysis, and minimizing the discomfort to the user, in which case a voltage of between about 0.05 and about 10 V is desirable, and a voltage of between about 0.1 and about 2 V is particularly desirable.

Although the above-described examples have been described in terms of a device and method for extracting glucose, the present invention may be applied to devices and methods for extracting other analytes, including but not limited to lactic acid, ascorbic acid, amino acid, enzyme substrate, drugs, and the like.

Although the devices embodying features of the present invention are constructed so as to extract analyte to the negative electrode side, they may also be constructed so as to extract analyte to the positive electrode side depending on the analyte to be extracted.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. An extraction device for extracting an analyte in living tissue through skin, the device comprising:

a first path-forming electrode part;

a first extraction electrode part for extracting an analyte;

a through-current electrode part; and a power supply part for supplying electrical energy to the first path-forming electrode part, the first extraction electrode part, and the through-current electrode part, for forming analyte transmission paths in the skin for the passage of the analyte, and for extracting the analyte at the first extraction electrode part;

wherein the first path-forming electrode part comprises a first path-forming electrode connected to the power supply part, and a first chamber comprising purified water/ion-conductive material, wherein the purified water/ion-conductive material contacts the first path-forming electrode;

wherein the first chamber is configured such that the purified water/ion-conductive material; is configured to contact the skin over an area of less than 25 mm²; and wherein, during formation of the analyte transmission paths, the first path-forming electrode part is connected to the power supply part; and wherein, during analyte extraction, the first path-forming electrode part is disconnected from the power supply part and the first extraction electrode part is connected to the power supply part.

2. The device of claim 1, wherein the power supply part supplies a current of less than about 300 μA.

3. The device of claim 1, wherein the purified water/ion-conductive material is configured to contact the skin-over an area of between 0.01 and 25 mm².

4. The device of claim 1, wherein the power supply part comprises a constant-current power supply.

5. The device of claim 1, wherein the power supply part comprises a constant-voltage power supply.

6. The device of claim 1, wherein the power supply part outputs a voltage of less than about 10 V.

7. The device of claim 1, further comprising an extraction accelerator part for promoting the extraction of the analyte.

8. The device of claim 7, wherein the extraction accelerator part comprises an ultrasonic irradiation part for irradiating the skin with ultrasonic waves.

9. The device of claim 1, wherein the analyte is glucose.

10. An analyzer for analyzing an analyte extracted through skin, the analyzer comprising:
the extraction device of claim 1;
an assay part for assaying the analyte extracted in the first electrode part, and for outputting a signal corresponding to an amount of the analyte;
an analysis part for analyzing the signal output by the assay part to obtain an analysis result; and
an output part for outputting the analysis result obtained by the analysis part.

11. The device of claim 1, wherein the contact area is between 0.01 and 25 mm².

12. The device of claim 1 further comprising:
a second path-forming electrode part; and
a second extraction electrode part for extracting an analyte;
wherein the power supply part comprises:
a first power supply for supplying electrical energy to the first path-forming electrode part, the first extraction electrode part, and the through-current electrode part, for forming analyte transmission paths in the skin, and for extracting analyte at the first extraction electrode part; and
a second power supply for supplying electrical energy to the second path-forming electrode part, the second extraction electrode part, and the through-current electrode part, for forming analyte transmission paths in the skin, and for extracting analyte at the second extraction electrode part;
wherein the second path-forming electrode part comprises:
a second path-forming electrode connected to the power supply part; and
a second chamber comprising purified water/ion-conductive material, wherein the purified water/ion-conductive material contacts the second path-forming electrode;
wherein the second chamber is configured such that the purified water/ion-conductive material has a contact area with the skin of less than 25 mm²; and mm
wherein, during formation of the analyte transmission paths, the second path-forming electrode part is connected to the power supply part; and
wherein, during analyte extraction, the second path-forming electrode part is disconnected from the power supply part and the second extraction electrode part is connected to the power supply part.

* * * * *